United States Patent [19]
Paoli

[11] Patent Number: 5,475,486
[45] Date of Patent: Dec. 12, 1995

[54] FLOW CELL SYSTEM FOR TURBIDIMETER

[75] Inventor: Ernie R. Paoli, Loveland, Colo.

[73] Assignee: Hach Company, Loveland, Colo.

[21] Appl. No.: 329,067

[22] Filed: Oct. 21, 1994

[51] Int. Cl.⁶ ..................................................... G01N 1/10
[52] U.S. Cl. ........................... 356/246; 356/440; 250/576
[58] Field of Search ................................... 356/246, 244, 356/410, 414, 440; 250/574, 576

[56] References Cited

U.S. PATENT DOCUMENTS

| 3,345,910 | 10/1967 | Rosin et al. | 356/246 |
|---|---|---|---|
| 3,508,837 | 4/1970 | Hrdina | 356/246 |
| 3,514,210 | 5/1970 | Hrdina | 356/246 |
| 3,582,222 | 6/1971 | Hoblik | 356/246 |
| 3,734,601 | 5/1973 | Heiss | 356/246 |
| 3,867,042 | 2/1975 | Mayer et al. | 356/246 |
| 3,871,770 | 3/1975 | von Behrens et al. | 356/246 |

Primary Examiner—Hoa Q. Pham
Attorney, Agent, or Firm—Dean P. Edmundson

[57] ABSTRACT

A flow cell system for use with a nephelometer (i.e., turbidimeter) to measure the turbidity of a liquid (e.g., water). The flow cell includes a transparent sample cell, an inlet port on the upper end of the cell, an outlet port on the upper end of the cell and another outlet port on the lower end of the cell. The upper outlet port collects and expels air bubbles and particles that tend to float in the sample. The lower outlet port collects and discharges settled solids. Measurement can be made on a dynamic (flowing) sample or a portion of the sample may be measured under static (non-flowing) conditions.

5 Claims, 4 Drawing Sheets

FLOW CELL SYSTEM FOR TURBIDIMETER

FIELD OF THE INVENTION

This invention relates to turbidimeters. More particularly, this invention relates to a sample flow cell for use in a laboratory turbidimeter.

BACKGROUND OF THE INVENTION

Turbidimeters have been known and used for decades for nephelometric measurement of color, turbidity, light absorbance and transmittance of liquids. Typically, a sample of the liquid to be tested is placed in a transparent glass cell which is then inserted into the instrument. A light beam is then directed through the cell and appropriate measurements are taken of the light scattering, absorbance and transmittance.

The greatest source of error (accuracy and non-reproducibility) in laboratory nephelometric measurement of sample turbidity (clarity) is sample cell variability and condition. Also, with single, individual sample cells, measurements of samples under dynamic flow conditions are not possible. Another source of error results from using different sample cells which may have different optical characteristics. Yet another source of error results from inherent cell flaws and scratches in the cell glass.

Although there have been previously proposed flow-through cell designs for use with a turbidimeter, such designs do not easily accommodate the need to measure a sample under either static or dynamic conditions. Rather, such designs are intended to operate either in a static condition or dynamic condition but not in both. Further, prior designs did not provide assurance that the system was completely purged of liquid sample, trapped or entrained air bubbles, and solid materials which are found in the sample.

Cells that have both the inlet and outlet in the top can collect heavy particles (which are not able to exit the cell). Cells that have both the inlet and outlet at the bottom collect bubbles and buoyant particles. Cells that have the inlet in the bottom and the outlet in the top collect heavy particles.

Some cells are extremely difficult to clean, and cleaning them consists of unscrewing barb fittings and disassembling "windows" in the cell. Thus, some cells require considerable amounts of maintenance.

The prior cells are not capable of siphoning the volume of sample out of them. Therefore, they require large amounts of DI water to purge or they require large amounts of DI water to purge the previous sample. Also, some cells have larger dead volumes and thus have slow response time.

Previous cell systems do not have the capability to be automatically (electronically) controlled by the instrument.

There has not heretofore been provided a flow cell system for a turbidimeter having the advantages and features provided by the present invention.

SUMMARY OF THE INVENTION

In accordance with the present invention there is provided an improved flow cell system for use with a nephelometer to measure the turbidity of a liquid (e.g., water). In one embodiment the flow cell comprises:

(a) a sample cell having a light transparent wall; wherein the cell has upper and lower ends;

(b) an inlet port on the upper end of the cell for introducing liquid into the cell; and (c) first and second outlet ports; wherein the first outlet port communicates with the upper end of the cell and the second outlet port communicates with the lower end of the cell.

The liquid sample is introduced into the top or upper end of the cell. Preferably a baffle deflects the sample to the side wall of the cell in order to minimize turbulence in the sample in the light path. The baffle also causes air bubbles to come out of solution by impingement and change of flow direction.

The liquid sample is discharged from the top and the bottom outlet ports. The top outlet port collects and expels air bubbles and particles that tend to float in the sample. The bottom outlet (preferably cone-shaped) collects settled solids. Liquid sample which is discharged from the bottom outlet carries the settled solids out of the cell.

The flow cell described herein eliminates dead volume in the cell to provide rapid, thorough flushing of the cell from one sample to the next.

Use of the flow cell system of the invention provides for increased speed of measurement. Also, because a single cell is used for all measurements, a constant optical path is always assured. This eliminates the need for providing optically matched cells. It also minimizes the amount of glassware that must be purchased, stored and cleaned.

Use of the flow cell system of this invention provides for accurate, reproducible and convenient measurement of sample color, turbidity, absorbance and transmittance at low pressures. The system can be used to monitor sample parameters for a static (non-flowing, fixed sample volume) or a dynamic (continuously flowing) sample. The system also increases the speed of analyzing multiple samples by simplifying the traditional measurement method of using multiple sample cells.

The flow cell system of the invention allows a laboratory turbidimeter to be used in a way that has traditionally been associated with process instruments. The turbidimeter can be programmed to automatically start and stop sample flow through the instrument with the flow valve module.

Also, the flow cell system of the invention can be plumbed rigidly (bypassing a sample reservoir and flow valve module), and the printer can be set up to record measurements at programmed intervals. These features enable the instrument to make and record dynamic measurements automatically.

When the flow cell is plumbed so as to receive the sample directly, it is not necessary to use the reservoir on the flow valve module.

Other advantages and features of the flow cell system of this invention will be apparent from the following detailed description and the accompanying drawings.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

Figure 1:
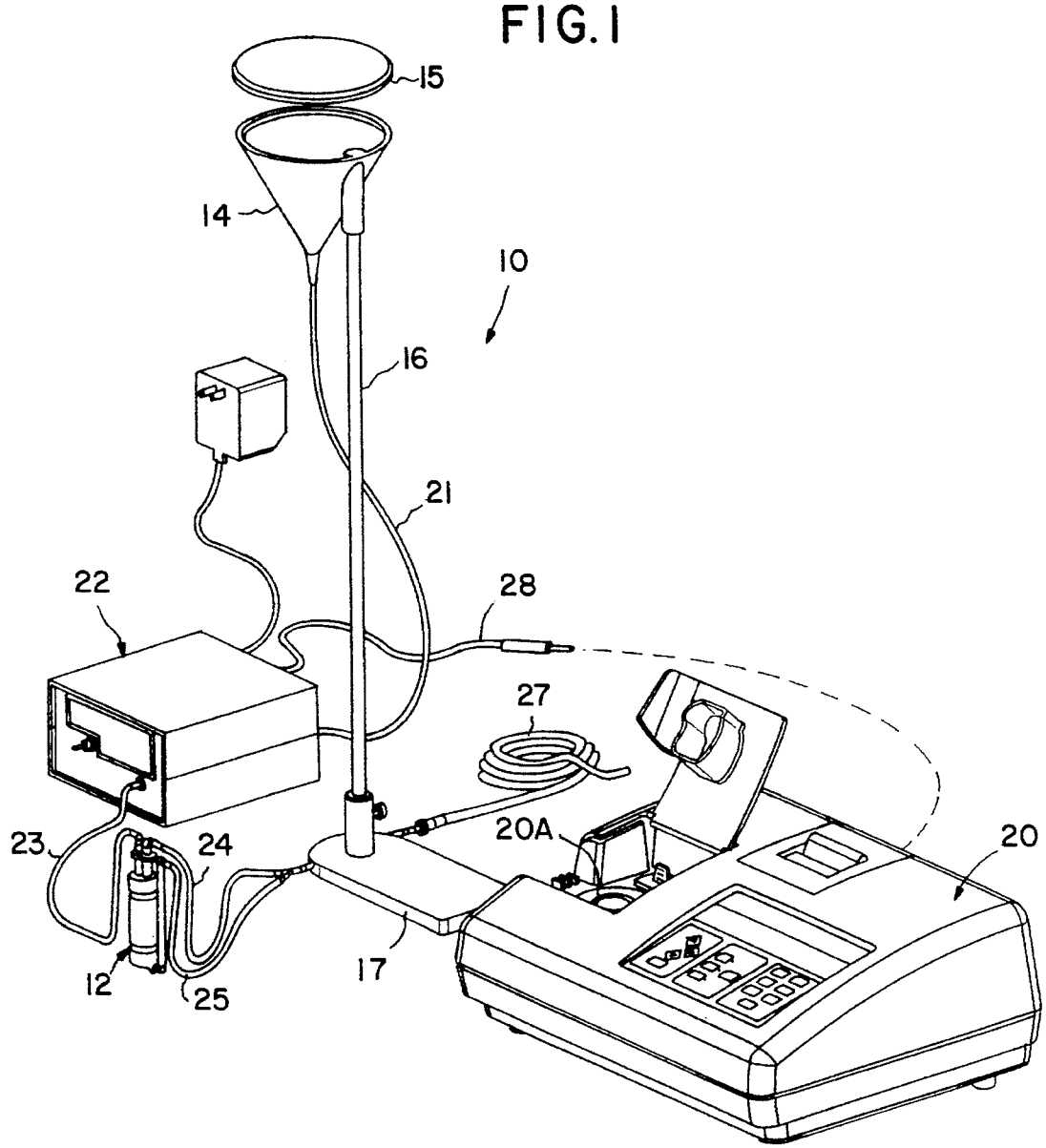
FIG. 1 is a perspective view of one embodiment of flow cell system of the invention.
Figure 2:
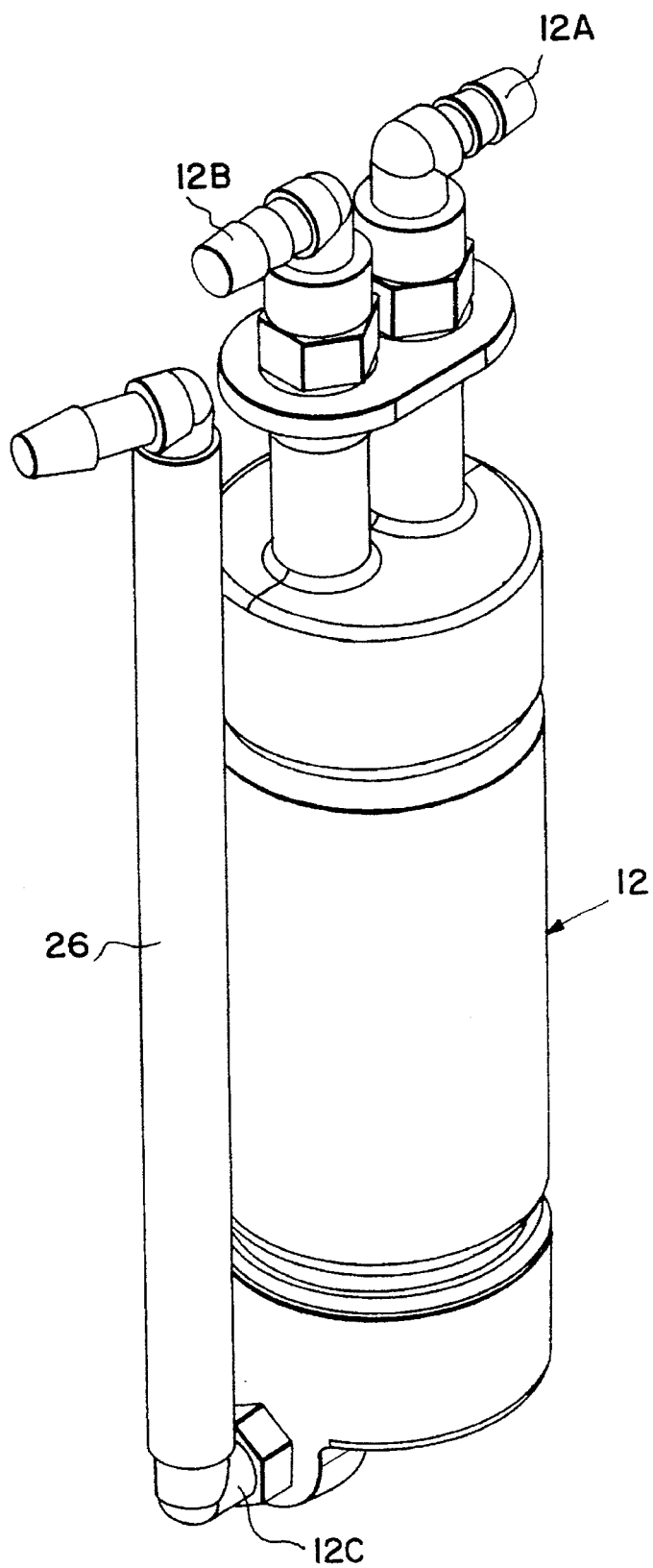
FIG. 2 is a perspective view of one embodiment of flow cell of the invention.
Figure 3:
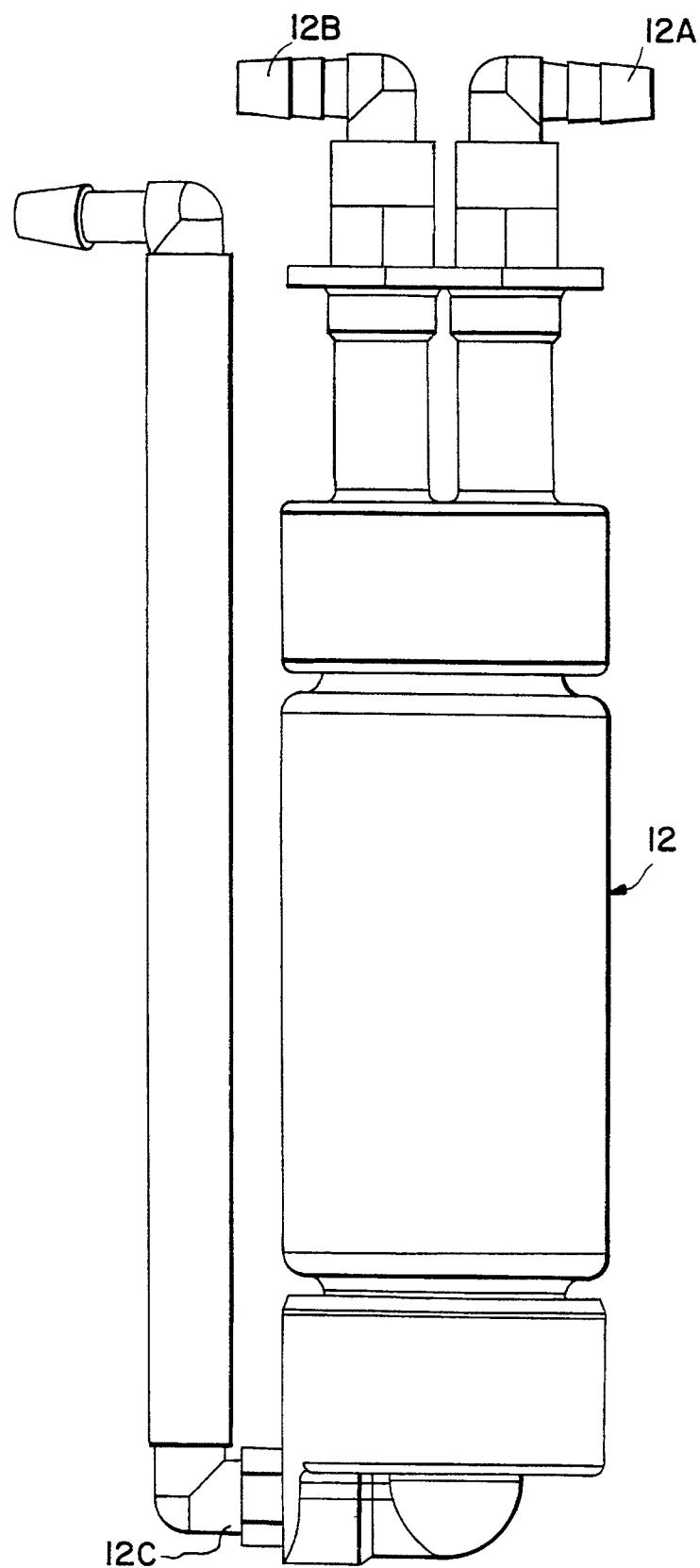
FIG. 3 is a side elevational view of the embodiment of flow cell of FIG. 2.
Figure 4:
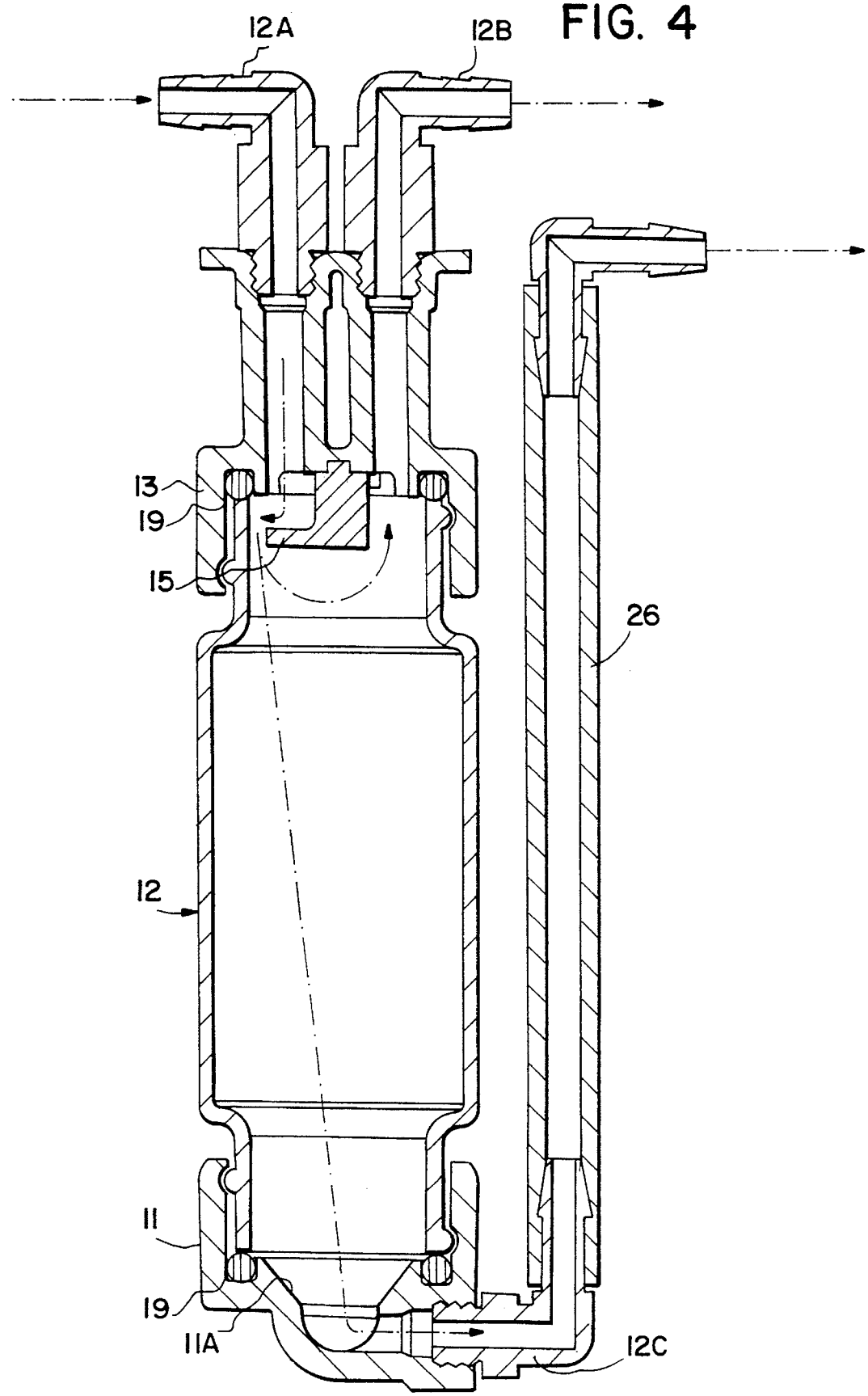
FIG. 4 is a cross-sectional view of the flow cell of FIG. 3.

In FIG. 1 there is shown one embodiment of a flow cell system 10 of the invention comprising a novel flow cell 12 which is connected between a turbidimeter or nephelometer 20 and a reservoir 14 containing liquid sample to be tested. A plastic cover 15 may be placed on the top of the conical reservoir to keep out dust and debris. The reservoir 14 is supported above the flow cell and the instrument by rod 16 held in base support 17.

Flexible conduit or tubing 21 extends from the outlet port at the base of the reservoir to a flow valve module 22. Tube or conduit 23 extends from the module to the inlet port 12A at the upper end of the flow cell 12. Tube 24 is connected to the outlet port 12B and tube 25 is connected to the extension line 26 from outlet port 12C at the lower end of the flow cell. Tubes 24 and 25 are both connected to a drain tube 27.

The function of the flow valve module (FVM) is to either automatically or manually control the flow of sample through the flow cell. The FVM is what permits the instrument to measure either static or dynamic sample. When the valve in the FVM is open, fluid can flow through the cell and at the end of the sample charge a siphon allows the cell to entirely drain. If the valve is shut after the cell has been filled with sample, all flow is stopped and a static measurement can be made.

The flow valve module basically comprises a solenoid pinch valve which is actuated either manually with a toggle switch located on the front panel of the FVM or automatically by the press of a key on the turbidimeter. A relay in the turbidimeter energizes the solenoid circuit by utilizing a wire 28 with phone jack connectors on both ends in which one end is connected to the remote jack on the turbidimeter and the other is connected to the flow valve module. The solenoid is powered by an external AC adapter. There is a bulkhead fitting on both the front and rear panel of the FVM which allows for the connection of tubing into and out of the FVM. Inside the FVM the bulkhead fittings have a piece of tubing connected between them and the pinch valve is situated such that the tubing passes through the pinch valve to enable it to pinch the tubing to stop the flow. The valve is normally closed, thus the circuit must be energized to allow fluid to pass through the FVM and flow cell. The toggle switch on the front panel is a three-position switch. When the switch is in the top position it puts the FVM in a continuous open mode of operation, and when the switch is in the middle location the valve is not energized and therefore closed. When the switch is in the bottom position it energizes the valve; however, the switch has a spring that always returns it from the bottom position to the middle position and therefore allows the valve to be momentarily open.

The flow cell 12 is intended to be slidably received in a cell port 20A in the turbidimeter 20. When the liquid sample enters the flow cell (when the flow cell is in the port 20A in the turbidimeter) any desired measurement of the liquid may be made. Measurement may be made while the liquid is in a static condition or in a dynamic condition.

Preferably the flow cell comprises a cylindrical glass body which is transparent to light. Other tubular shapes for the flow cell may also be used. Preferably the upper and lower ends of the body are threaded so that a threaded cap 11 can be threaded onto the lower end and a threaded cap 13 can be threaded onto the upper end. Other types of fastening means may also be used, if desired, for securing the cap members to the glass body. For example, it is possible to use snaps, bayonet fasteners, etc.

Cap 13 includes a baffle 15 which directs incoming liquid sample toward the side wall of the flow cell. The impingement of the sample on the baffle and the cell wall facilitates the separation of entrained gas bubbles and saturated gas from the sample liquid and minimizes turbulence in the optical region of the sample cell. This impingement also allows the bubbles to remain near the surface of the fluid rather than being forced toward the bottom of the cell. Thus, the accumulation of bubbles is minimized.

The design of the flow cell also eliminates accumulation of solids that settle out of solution. The flow cell includes a drain in the bottom end cap 11 which allows the cell to discharge the sample and dense, insoluble particles which would normally be trapped in the cell. This discharge of dense insoluble particles is aided by the conical-shaped surface 11A at the bottom end cap. The bottom drain also enables the cell to be completely purged.

Preferably the upper and lower cap members are made of light-absorbing material to minimize stray light in the instrument. The placement of the inlet and outlet tubes in the end cap members also minimize stray light. This facilitates use of the flow cell of this invention for ultra-low measurements.

The flow cell system of this invention has the ability to operate under both manual control or remote control from an external device which permits a programmable time for filling and purging the system as well as programmable times for sample measurement. Programmability of sample measurement times permits the study of sample measurements vs. time to determine sample stability or reaction rates.

Operation of the bottom drain via a siphoning effect is also unique. Conventional flow-through cells have only a single top discharge which is ineffective in removal of gases and solids, and such cells cannot be effectively purged of sample after a measurement is taken. A long purge time results in a slow response time.

Another advantage of the flow cell of this invention is the ease of cleaning. The end cap members are easily removed. O-rings 19 between the cap members and the glass cell body seal the cap members. The glass body can be simply soaked in solution to enhance cleaning.

Yet another advantage of the flow cell is that it can be completely purged with a relatively small volume of liquid sample (about 120 ml). It is very difficult to purge conventional flow cells to remove settled and suspended particles.

The flow cell of this invention is also very easy to use. This enables the speed of measurements to be significantly increased. The flow cell is designed to operate at low pressure.

Other variants are possible without departing from the scope of this invention.

What is claimed is:

1. A flow cell system for use with a nephelometer, the system comprising:

(a) a sample cell having a light transparent wall; wherein said cell has upper and lower ends;

(b) an inlet port on said upper end of said cell for introducing liquid into said cell; and (c) first and second outlet ports; wherein said first outlet port communicates with said upper end of said cell, and wherein said second outlet port communicates with said lower end of said cell; and (d) baffle means in said upper end of said cell for directing liquid entering through said inlet port against said wall.

2. A flow cell system in accordance with claim 1, wherein said cell is cylindrical.

3. A flow cell system in accordance with claim 1, further comprising a sample reservoir having an outlet connected with a conduit to said inlet port on said upper end of said cells.

4. A flow cell system in accordance with claim 3, further comprising a flow valve in said conduit for regulating flow of said liquid sample from said reservoir to said sample cell.

5. A flow cell system in accordance with claim 1, wherein said upper and lower ends of said cell are threaded; and further comprising upper and lower threaded cap members which are threadably secured to said upper and lower ends of said cell.

* * * * *